United States Patent [19]

Kovacs

[11] Patent Number: 5,749,839
[45] Date of Patent: May 12, 1998

[54] DIRECT MECHANICAL BI-VENTRICULAR CARDIAC ASSIST DEVICE

[75] Inventor: Stephen G. Kovacs, Durham, N.C.

[73] Assignee: Duke University, Durham, N.C.

[21] Appl. No.: 655,310

[22] Filed: May 21, 1996

Related U.S. Application Data

[63] Continuation of Ser. No. 292,726, Aug. 18, 1994, abandoned.

[51] Int. Cl.$^6$ ............................................. A61H 31/00
[52] U.S. Cl. ............................................. 601/153; 600/16
[58] Field of Search .......................... 601/151-3; 623/3; 600/16, 17

[56] References Cited

U.S. PATENT DOCUMENTS

| | | |
|---|---|---|
| 2,826,193 | 3/1958 | Vineberg ............................ 601/153 |
| 3,034,501 | 5/1962 | Hewson . |
| 3,053,249 | 9/1962 | Smith ................................. 601/153 |
| 3,233,607 | 2/1966 | Bolie . |
| 3,279,464 | 10/1966 | Kline . |
| 3,371,662 | 3/1968 | Heid et al. . |
| 3,376,863 | 4/1968 | Kolobow et al. ................... 601/153 |
| 3,455,298 | 7/1969 | Anstadt ............................... 601/153 |
| 3,478,737 | 11/1969 | Rassman . |
| 3,587,567 | 6/1971 | Schiff ............................. 601/153 X |
| 3,590,815 | 7/1971 | Schiff . |
| 3,613,672 | 10/1971 | Schiff ............................. 601/153 X |
| 4,048,990 | 9/1977 | Goetz ................................. 601/153 |
| 4,192,293 | 3/1980 | Asrican . |
| 4,506,658 | 3/1985 | Casile . |
| 4,536,893 | 8/1985 | Parravicini ..................... 601/153 X |
| 4,621,617 | 11/1986 | Sharma . |
| 4,690,134 | 9/1987 | Snyders ............................. 601/153 |
| 4,731,076 | 3/1988 | Noon et al. . |
| 4,809,684 | 3/1989 | Gardner et al. . |
| 4,922,893 | 5/1990 | Wright et al. . |
| 5,119,804 | 6/1992 | Anstadt ............................... 601/153 |
| 5,169,381 | 12/1992 | Snyders ......................... 601/153 X |
| 5,273,518 | 12/1993 | Lee et al. . |
| 5,429,584 | 7/1995 | Chiu . |

FOREIGN PATENT DOCUMENTS

| | | | |
|---|---|---|---|
| 2 321 266 | 3/1977 | France . | |
| 0200117 | 7/1967 | U.S.S.R. ......................... 601/153 |

OTHER PUBLICATIONS

Walcott and Wherry, *Surgery*, Nov., 1960 pp. 903-906.

*Primary Examiner*—Danton D. DeMille
*Attorney, Agent, or Firm*—Nixon & Vanderhye P.C.

[57] ABSTRACT

A direct mechanical bi-ventricular cardiac assist device comprises a ventricular actuation cup having two independently operated diaphragms for independently actuating the right and left ventricle of the patient's heart. The pressure and timing of each diaphragm can be independently varied to maximize forward cardiac output. The ventricular actuation cup is constructed in two components including a main body section and an end piece. The diaphragm wraps around the ends of the main body section and the edges of the diaphragm are bonded to the outer surface of the main body section. Bonding of the diaphragm to the outer surface of the ventricular actuation cup eliminates lifting and tearing vectors which could result in diaphragm failure.

18 Claims, 4 Drawing Sheets

DIRECT MECHANICAL BI-VENTRICULAR CARDIAC ASSIST DEVICE

This is a continuation of application Ser. No. 08/292,726, filed Aug. 18, 1994, now abandoned.

FIELD OF THE INVENTION

The present invention relates generally to the field of cardiac assist devices, and more particularly, to a direct, mechanical, bi-ventricular cardiac assist device for mechanically actuating the ventricles of the patient's heart.

BACKGROUND OF THE INVENTION

It is common practice today to use mechanical devices to maintain a supply of oxygen and blood circulation during heart failure. One type of device used for this purpose is known as the heart-lung machine. A heart-lung machine performs the function of the heart and lungs. Venous blood is removed from the patient's body and passed through an external oxygenator. The oxygenated blood is then returned to the patient's body. Heart-lung machines are frequently used during open-heart surgery to maintain a supply of oxygen and blood circulation.

Another method which is used to maintain blood circulation is a ventricular actuation cup. These devices typically comprise a cup which fits around the human heart. A thin membrane is bonded to the inner surface of the cup and functions as a diaphragm. Positive and negative pressure is applied to the space between the membrane and the cup wall to alternately inflate and deflate the diaphragm. When the diaphragm is inflated, the heart is squeezed to simulate systolic action. Similarly, when the diaphragm is deflated, the heart muscle relaxes to simulate diastolic action.

The ventricular actuation cups described above have been proven effective in the treatment of patients subject to heart failure. The blood circulation of such patients can be maintained for periods up to several weeks with such devices. However, ventricular actuation cups have some drawbacks.

One frequently encountered problem with the present ventricular actuation cups currently in use relates to the possibility of the failure of the diaphragm. In prior art designs, the diaphragm is bonded to the inner surface of the cup. During the systolic pumping phase, the diaphragm is progressively distended. Several stress factors localized at the bond zones are significantly increased in magnitude. The stress factor associated with a lifting or tearing force at the bond zone reaches its maximum value at maximum systolic distention. This lifting/tearing vector tends to separate the membrane from the cup wall. Continued cyclic development of this stress vector may lead to bond failure which renders the device inoperative. When a bonding failure occurs, the patient's life becomes seriously threatened.

Another significant drawback of currently available ventricular actuation devices is that right and left ventricle pumping is accomplished by using a single diaphragm. As a result, it is difficult to simulate the normal heart function. It is well established that differences exist between right and left ventricle output. It is known, for instance, that right and left ventricular pressures are different. Normal ventricle pressures are 120 over 12-15 mm Hg for the left ventricle and 25-30 over 0-5 mm Hg for the right ventricle. As a result, the pressure selected for ventricular actuation will, at best, be a compromise between the optimum pressure for either the left or right ventricle. Any adjustment of left ventricular flow or pressure will alter right ventricular pumping parameters. Thus, it is virtually impossible to achieve optimum output and pressures for both the right and left ventricle using a single diaphragm.

The design of currently available ventricular actuation cups also leads to trauma of tissue and organs surrounding the heart. Most cups have a large port molded to the outer surface of the cup which is used for actuation of the diaphragm. When the cup is positioned to contain the heart, the combined reaction to the continuous systolic/diastolic pumping action causes the cup to continually oscillate about its longitudinal axis. The magnitude of this longitudinal oscillation can vary from as much as +15° to −15°. As the device oscillates, the relatively high profile inlet port rubs against surrounding tissue and lungs. The continuous rubbing or abrasion of lung tissue may lead to progressive development of atelectasis in which the alveolar cells in the traumatized lung tissue collapse. In the most serious cases, the continuous trauma has resulted in pulmonary bleeding with resultant pulmonary function compromise.

Another consideration that existing ventricular actuation cups often fail to take into account is the variation in size of the human heart from one person to another. Furthermore, it is possible that different size cups may be needed for the same patient. Certain physiological conditions, such as pulmonary hypertension can result in dilation of the heart. When the ventricular actuation cup is initially placed, a relatively large cup may be needed to accommodate the dilated heart. As the heart returns to a more normal size, the efficiency of the oversize cup in maintaining blood circulation may diminish to the point that a smaller cup must be used. This problem is usually addressed by manufacturing cups of different size to accommodate different size hearts. The surgeon must therefore have a relatively large number of differently sized cups on hand to select from depending on the size of his patient's heart and the patient's physiological condition.

Current univentricular devices, e.g. Anstadt, U.S. Pat. No. 5,119,804, presently use a rotary vane combination pressure-vacuum pump as the common source for obtaining and maintaining the pressures and vacuums required for systolic and diastolic ventricular cup actuation. Systolic and diastolic pumping action times are essentially controlled by a combination of timers operating solenoid valves in both the pressure and vacuum lines such that the single drive line delivers a timed sequence of diaphragm distending systolic pressure pulses and diaphragm retraction diastolic vacuum pulses.

An unavoidable requirement in this type of drive line source is a mechanical device called a "damper valve" in the primary drive line exiting the sequencing pressure-vacuum manifold. This valve serves the primary function of "damping" the transition from systolic-diastolic pumping action, in order to prevent diaphragm "slap" during diastolic relaxation. The damper valve is also used in establishing the pressure profile of systolic pumping action—e.g. applying during early systolic compression approximately 25-30 mm.Hg and during late systolic compression approximately 120-150 mm Hg. Similarly, during the diastolic phase of each cycle, vacuum pressures of approximately −100 to −120 mm Hg are applied.

The requirement of the damping valve for purposes just set forth totally prohibits simultaneous and independent control of both left and right ventricular pumping action, in terms of required physiological flow rates and pressures, and related to patient forward flow requirements of a changing nature with time.

SUMMARY AND OBJECTS OF THE INVENTION

The present invention is a bi-ventricular assist device for maintaining blood circulation in a patient having a minimally functioning or malfunctioning heart. The bi-ventricular assist device comprises a ventricular actuation cup which fits over the patient's heart, and at least one annular diaphragm along the inner wall of the cup which provides ventricular actuation. Ventricular actuation is accomplished by alternately applying positive and negative pressures to the diaphragm chamber to simulate systolic and diastolic action. When positive pressure is applied, the diaphragm distends and compresses the heart to simulate systole. When negative pressure is applied, the diaphragm contracts allowing the heart muscle to relax simulating diastole.

The ventricular actuation cup of the present invention employs a novel configuration to prevent failures, particularly at the bond zones. The cup is constructed in two parts including a main body section and an end piece. The main body section includes a distal end which defines the cup opening and a proximal end. The diaphragm is disposed adjacent the inner surface of the main body section and wraps around the ends of the main body section. The ends of the diaphragm are then bonded to the outer surface of the main body section. After attaching the diaphragm to the main body section, the end piece is bonded to the proximal end of the main body section to form the closed end of the cup. This construction eliminates the lifting vector which has been associated with bond failures in prior devices. As a result, a substantial increase in reliability and patient safety is obtained. Further, this design eliminates the "dead zone" in prior art designs which are required for bonding the diaphragm to the inner wall of the cup. As a result, the membrane area available for ventricular actuation is increased.

In a preferred embodiment of the invention, two semi-annular diaphragms are disposed within the cup to allow independent right and left ventricular actuation. Each semi-annular diaphragm corresponds in sector angle size to the nominal sector angle size of both the right and left ventricle of the natural heart, by having two independent annular diaphragms, it is possible to achieve simultaneous and independent control of both left and right ventricular actuation. Independent control of right and left ventricular actuation enables the surgeon to optimize forward cardiac output by applying different pressures to the right and left ventricle. Further, independent right and left ventricular actuations provides a means for surgeons to compensate for abnormal physiologic conditions such as pulmonary hypertension.

The use of two semi-annular diaphragms also provides a safety feature which cannot be provided by single diaphragm cups. In single diaphragm cups, a tear or rupture of the diaphragm renders the cup inoperative and creates a life-threatening emergency for the patient. In the present invention, the failure of one diaphragm can be compensated by increasing pressure of the remaining diaphragm. The increased pressure of the remaining diaphragm would permit the patient to be sustained with a level of circulatory support sufficient to permit surgical intervention for removal and replacement of the failed cup.

Also, in a preferred embodiment of the invention, the cup may be provided with an inflatable compensation ring which helps retain the heart within the cup during operation. The inflatable compensation ring can be inflated, for example, by injecting a saline solution or silicone gel into the compensation ring. The degree of inflation of the ring will depend on the size of the human heart contained in the cup. This improvement enables a single cup to accommodate a greater range in sizes of human hearts.

Other objects and advantages of the present invention will become apparent and obvious from a study of the following description and the accompanying drawings which are merely illustrative of such invention.

DETAILED DESCRIPTION OF THE INVENTION

Overview

Figure 1:
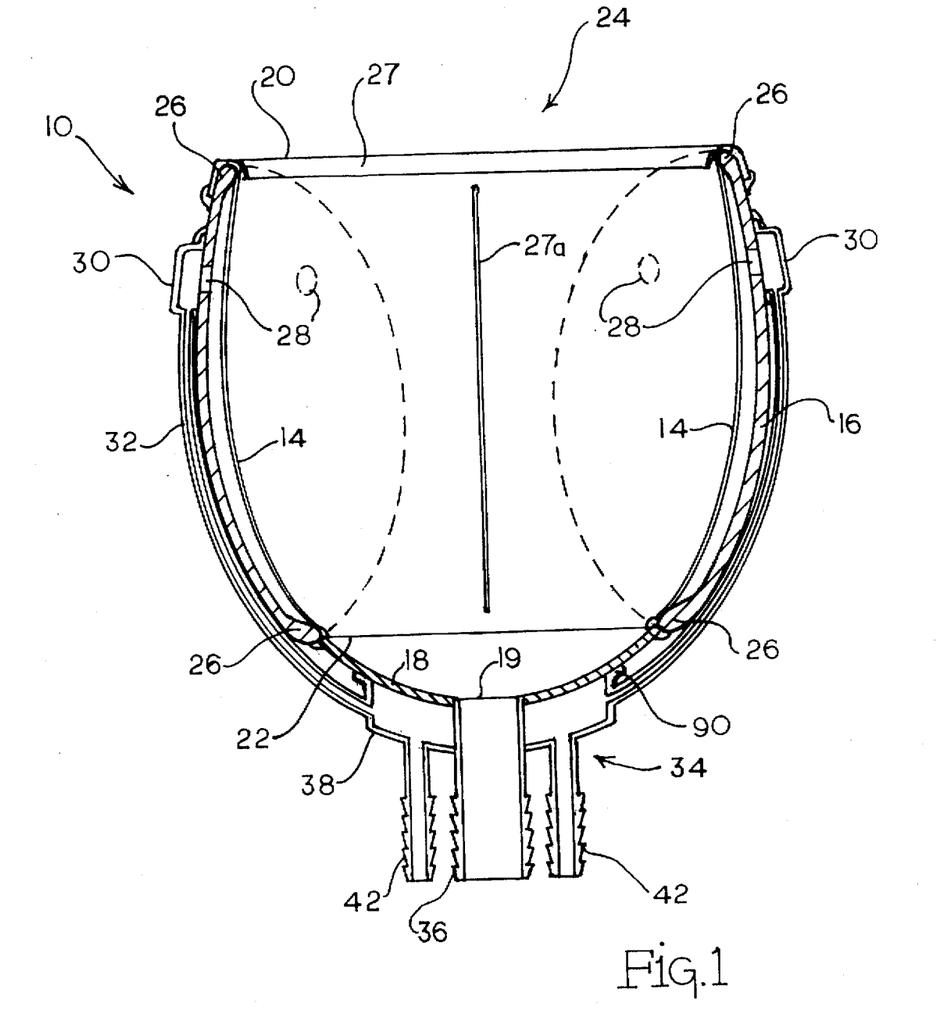
FIG. 1 is a section view of the biventricular actuation device.
Figure 2:
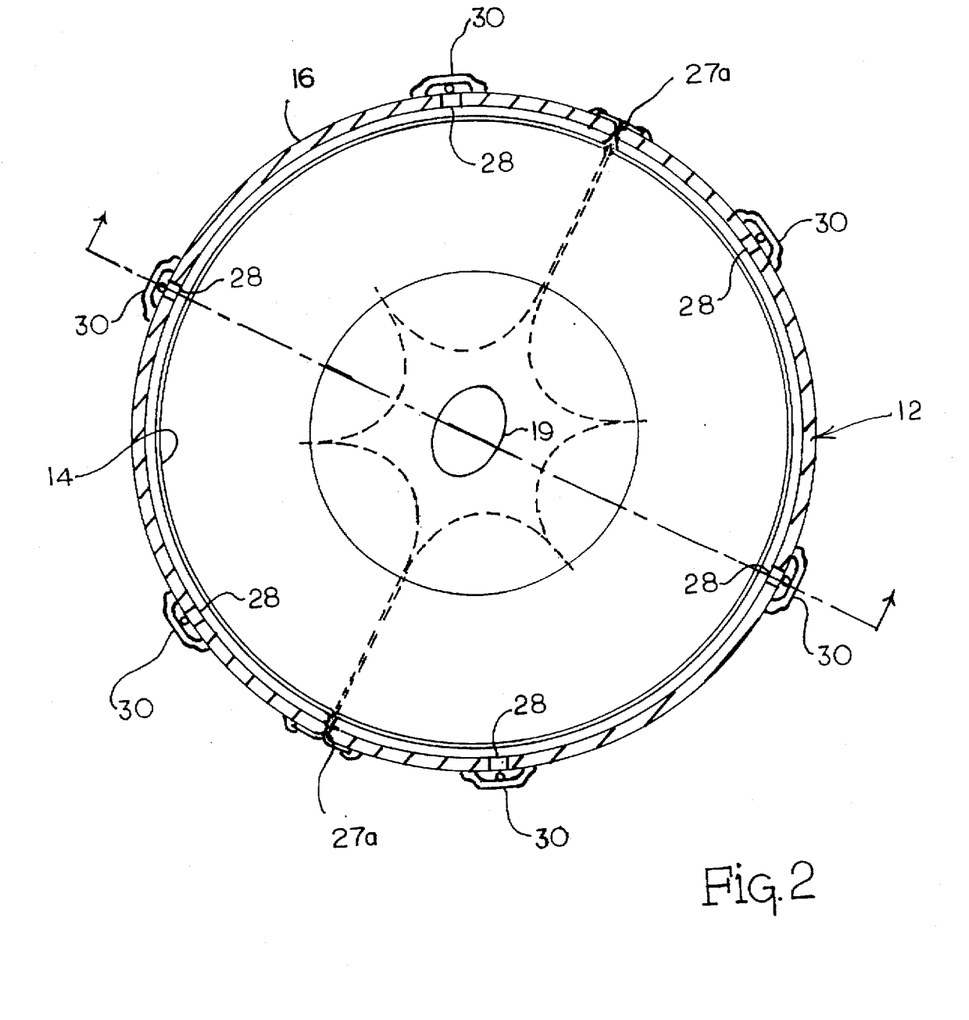
FIG. 2 is a cross-section view of the biventricular actuation device taken through line 2—2 of FIG. 1.

Referring now to the drawings, the biventricular assist device of the present invention is shown therein and indicated generally by the numeral 10. The biventricular assist device comprises a generally parabolic-shaped cup 12 having two semi-annular diaphragms 14 disposed adjacent to the inner surface of the cup 12. The cup 12 is sized to fit over the human heart. The diaphragms 14 are actuated by applying positive and negative pressure to the space between the diaphragms 14 and the cup wall. As the diaphragms 14 inflate or distend, the heart is compressed to empty the right and left ventricles of the heart. When the diaphragms 14 deflate, the heart muscle relaxes allowing blood to flow into the ventricles.

Cup Design

The cup 12 is constructed in two components—a main body section 16 and an end piece 18. The diaphragms 14 are bonded to the main body section 16 as will be hereinafter described and then the end piece 18 is bonded to the main body section 16 to form the cup 12. All components are made of a urea-linked polyureathane copolymer. All bonding is done using liquid polymer of the same formulation. After the bonding polymer is applied and allowed to cure, no seams exist since the bonding polymer and the two sections become homogeneous and isotropic upon cure due to identical material formula.

The main body section 16 includes a distal end 20 and a proximal end 22. The main body section 16 should preferably have a Shore A hardness in the range of 70–82, and more preferably in the range of 70–75. The distal end 20 defines a cup opening 24. Rounded lobes 26 are formed adjacent both the distal end 20 and the proximal end 22.

Figure 3:
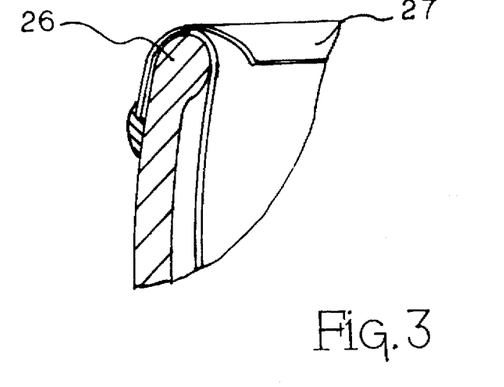
FIG. 3 is a detailed section view illustrating the method of attachment of the diaphragm.

Each diaphragm 14 is disposed adjacent the inner surface of the main body section 16 of the cup 12 and extends approximately 180° around the inner surface of the cup. The ends of the diaphragm 14 are wrapped around the lobes 26 at both ends and then liquid polymer isotropic bonded to the outer surface of the main body section 16. The side edges of the diaphragms 14 extend through slots 27 a in the main body section 16 and are disposed against the outer surface of the main body section as seen best in FIG. 2. The common formula bonding agent is applied between the edge portions of the diaphragm 14 and the main body section 16. An overcoat of the same common formula bonding agent is then applied to seal the edges of the diaphragm 14. When cured, no physical seams exist due to isotropic bonding.

After the diaphragms 14 are bonded to the main body section 16, the end piece 18 is then bounded to the proximal end 22 of the main body section 16. The end piece 18 has a Shore A hardness of approximately 58–60. A central opening 19 is formed in the center of the end piece 18. The liquid polymer isotropic bonding agent is applied to the edge of the end piece 18 where it joins the main body section 16. An overcoat of same liquid polymer is then applied to both sides of the joint between main body section 16 and the end piece 18. Again, no seams exists due to isotropic bonding.

A flexible annular flange 27 is finally polymer bonded to the distal end of the cup assembly. This flange, approximately ⅜ wide and 0.018" thick, is angled inward at an angle of 15–20°. It functions as a vacuum seal between the heart and the cup 12, in order to prevent the heart from being ejected during systolic compression.

Figure 4:
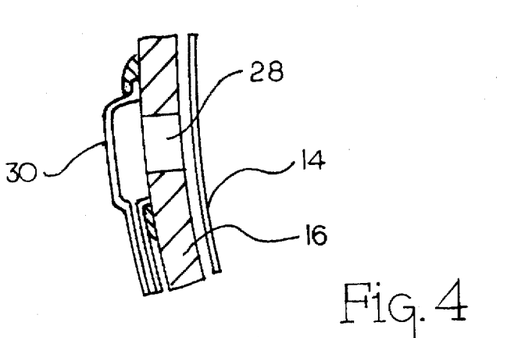
FIG. 4 is a detailed section view illustrating the method of attaching the manifold.

A series of inlet openings 28 are formed in the main body section 16 of the cup 12. In the disclosed embodiment, six openings are formed a fixed distance from the distal end 20. These inlet openings 28 communicate with each diaphragm chamber. A series of manifolds 30 are attached to the outer surface of the cup 12 and enclose the inlet openings 28. The manifolds 30 are connected by pressure lines 32 to a drive connector 34 which is liquid polymer bonded to the base of the end piece 18. The drive connector 34 is connected to a pressure system for applying positive and negative pressures to actuate the diaphragm 14.

The manifolds 30 have a generally flat profile with smooth mold blended contours. A flange is formed around the perimeter of each manifold 30 to facilitate bonding the manifold 30 to the outer surface of the main body section 16. The interior of the manifold defines an elongated oval-shaped space which communicates with the inlet openings 28 in the main body section 16. After the end piece 18 is fixed to the main body section 16, the manifolds 30 are bonded to the outer surface of the main body section 16. The bonding agent is applied to the bottom surface of the flanges 32 and the manifolds 30 are pressed against the outer surface of the main body section 16. An overcoat is then applied to the flange.

Figures 5, 6B:
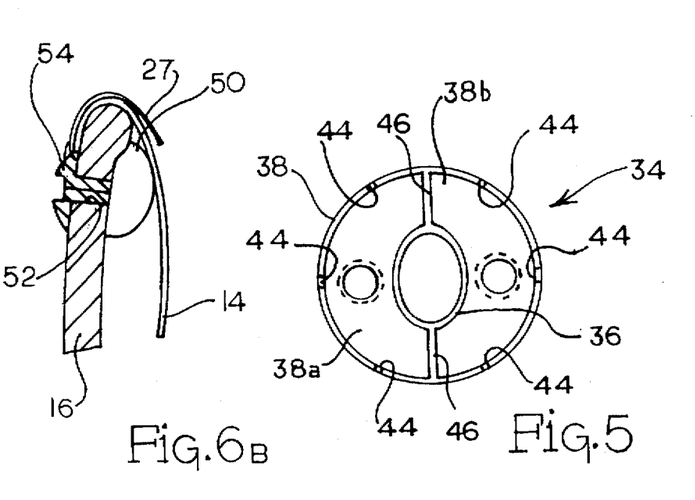
FIG. 5 is a cross section of the connector.
FIGS. 6a and 6b are detailed sections showing the optional compensation ring.

Referring now to FIG. 5, the biventricular drive connector 34 is shown. The drive connector 34 includes an elliptical center tube 36 and an outer housing 38. The outer housing 38 is divided by a web 46 into two distribution chambers 38a and 38b. The two distribution chambers 38a and 38b function as two, completely independent pressure/vacuum manifolds. These manifolds serve to connect the bi-ventricular cup 12 to the drive lines which independently drive the semi-annular right and left ventricle pumping diaphragms. A flange (not shown) extends outwardly from the upper end of the housing 38 for bonding the drive connector 34 to the end piece 18. Two inlet tubes 42 project downwardly from the housing 38 on opposite sides of the center tube 36. A series of outlet openings 44 are formed in the housing 38.

The connector 34 is bonded to the apex of the end piece 18 such that the center tube 36 communicates with the opening 19 in the center of the end piece 18. The liquid polymer isotropic bonding agent is applied to the surface of the flange 42 and to the end of the center tube 36 to bond the drive connector 34 to the end piece 18. The liquid polymer isotropic bonding agent is then applied as an overcoat to the flange 42 to form a smooth transition from the surface of the end piece 18 to the flange 42.

Pressure lines 32 connect each manifold 30 to a respective distribution chambers 38a or 38b of the drive connector 34. The right distribution chamber 38a of the connector 34 is connected by three separate pressure lines 32 to respective manifold parts 30 on the right side of the cup 12. Three additional pressure lines 32 connect the left distribution chamber 38b of the drive connector 34 to the manifold parts 30 on the left side of the cup 12. The pressure lines 32 extend from the outlet openings 44 in the connector to an inlet opening in the manifolds 30. The pressure lines 32 are then affixed to the outer surface of the cup 12 by applying the liquid polymer isotropic bonding agent to overcoat the pressure lines 32.

Figure 6A:
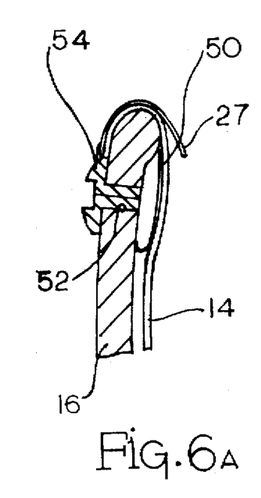

FIGS. 6a and 6b illustrate an optional compensation ring 50 which may be incorporated into the biventricular assist device 10. The compensation ring 50 comprises an annular membrane fixed to the main body 16 adjacent the distal end 20. The compensation ring 50 is disposed between the main body 16 and the diaphragm 14. An opening 52 is fitted with a conventional fill valve 54. Fluid can be injected into the compensation ring 50 through the fill valve 54 to inflate the compensation ring 50. It will therefore be appreciated that the compensation ring 50 allows the size of the cup opening 24 to be adjusted depending on the size of the patient's heart.

Materials

Various elastomers, polymers, and plastics have been developed and are readily available for human tissue and organ prothesis. These materials typically include SILASTIC, BIOMER, PELLATHANE, POLYSILOXANES, and COROTHANE. Various formulations of these materials may be used in the fabrication of the bi-ventricular assist device 10.

A copolymer comprising a urea-linked, cast, block finish, thermostat polyureathane is particularly well suited for the present invention. These polymers comprise a mixture of oligomeric di-mono-amino benzoates prepolymers modified with diphenylmethane di-isocyanate, (MDI) polymerizers and chain extenders, and appropriate reaction and material characteristic modifiers. All of these components are widely available from various commercial sources.

Oligomeric mono-and di-amino benzoates are useful in polyurethane cast elastomers because their reactivity is different from that of other MDI amino formulations commonly used in reaction injection molding (RIM) applications. Conventional approaches to the preparation of cast elastomers involve the reaction of a short chain diamine with a long chain polymer terminated with toluene di-isocyanate. Another commonly used system involves reacting diols with resins capped with MDI or methylene di-isocyanate, or methylene-bis-p-phenyl-isocyanate. Oligomeric mono and di-amino benzoates reverse the typical arrangement of the reacting agents resulting in the amine functionality being capped onto the ends of the soft segment. Chain extension is accomplished by using MDI, modified forms of monomeric MDI, or MDI containing resins as the hard segment. Elastomers prepared using these methods were determined as exhibiting the best overall physical properties for practicing the present invention. The formulation of these components to obtain a urea-linked polyureathane co-polymer is governed by the well-principled science of stoichiometric chemistry. Stoichiometric chemistry mix requirements for compatible polymer components of various average molecular weight and various NCO % content are well known and practiced by those skilled in the science of polymer chemistry.

Drive Mechanics

Figure 7:
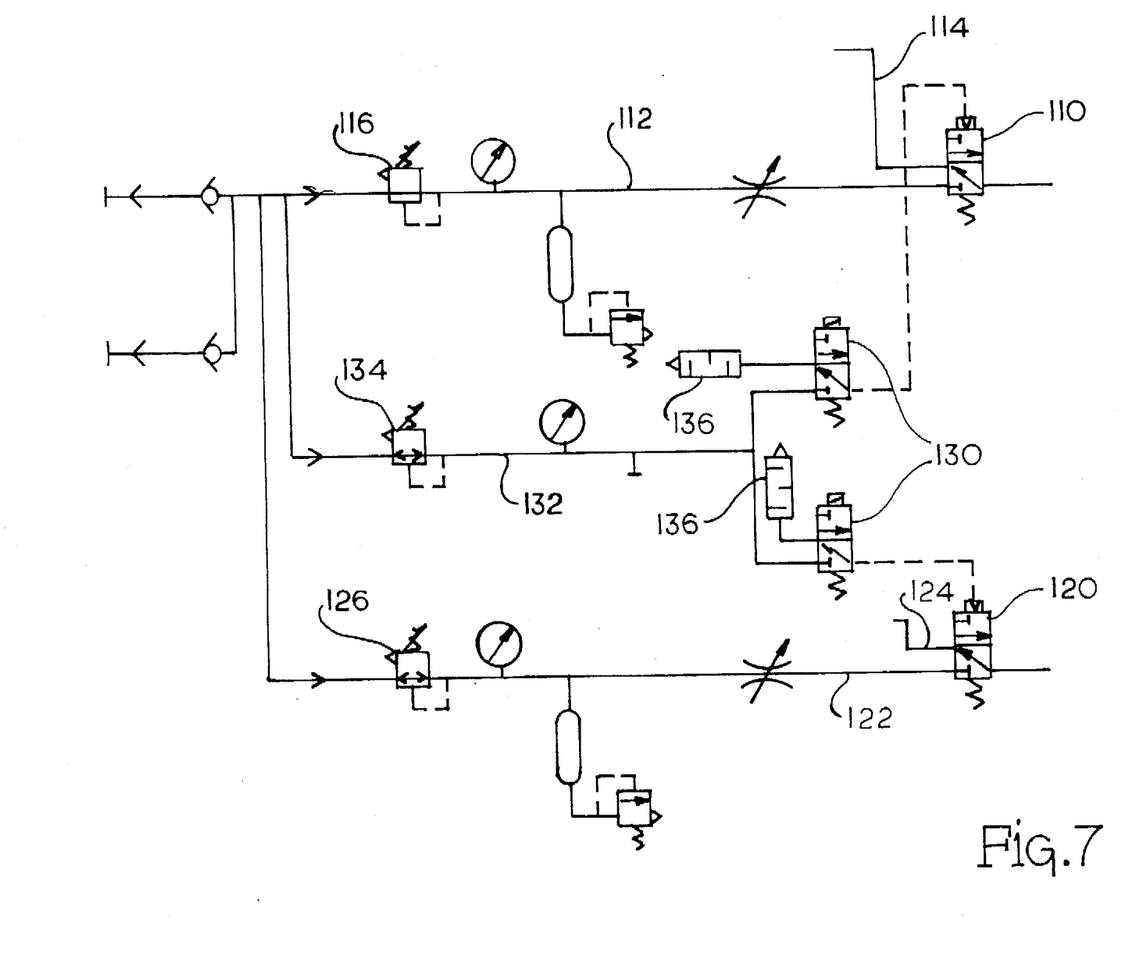
FIG. 7 is a schematic diagram the pulsed pressure system for the biventricular assist device.

The ventricular actuation cup 12 is actuated by a conventional pulsed-pressure system indicated generally by the numeral 100. The pulse pressure system includes both a systolic pressure source for applying a positive pressure to the diaphragm 14 and a diastolic vacuum source 120 for applying negative pressure to the diaphragm chamber. The systolic pressure source can be independently regulated to obtain a peak output in the range of 120 to 200 mm of Hg. The diastolic vacuum source can be independently regulated to obtain a peak negative pressure of approximately 40 to 100 mm of Hg.

The pressure system also includes a constant negative pressure system (not shown). The constant negative pressure system comprises an independently controllable vacuum source which is connected to the center tube 36 of the drive connector 34. The vacuum source applies negative pressure to the interior of the ventricular actuation cup 12 to help maintain the heart within the cup 12. The vacuum source should preferably apply a pressure in the range of 25 mm of Hg to 60 mm of Hg.

FIG. 7 is a schematic diagram of the pulsed pressure system for the biventricular assist device 10. The drive lines for the biventricular assist device are connected to valves 110 and 120. The drive lines for the right ventricle is connected to valve 110 while the drive line for the left ventricle is connected to valve 120. Each of the valves 110 and 120 are connected to the positive pressure source and the negative pressure source. Valve 110 is connected by positive pressure line 112 to the positive pressure source and by negative pressure line 114 to the negative pressure source. Similarly, valve 120 is connected by positive pressure line 122 to the positive pressure source and by negative pressure line 124 to the negative pressure source. Pressure regulators 116 and 126 regulate the pressure in lines 112 and 122 respectively.

Valves 110 and 120 are conventional two position Humphrey valves. During operation, the valves 110 and 120 constantly shift position to provide positive and negative pressure pulses to their respective drive lines. A pair of pilot valves 130 are used to shift the position of the valves 110 and 120. The pilot valves are connected by line 132 to the positive pressure source. A pressure regulator 134 is disposed in line 132 to regulate the pressure. Positive pressure is directed through the pilot valves 130 to the valves 110 and 120. The pilot valves 130 are actuated by mechanical actuators 136 so that each time the pilot valves 130 shift, its corresponding valve 110 or 120 shifts position. The actuators 136 for the pilot valves 130 can be independently controlled so that the timing of the positive and negative pressure pulses for each of the valves 110 and 120 can be independently controlled.

In the present invention, the systolic pressure source and the diastolic vacuum source are separate and independent, effectively, eliminating recurrent manual damper valve "tuning" adjustments required for changing cardiac assist needs. The pulsed pressure system permits independent LVAD and RVAD cardiac support with the desirable feature of independent left and right ventricle systolic and diastolic pressure vacuum profile controls.

Although "air" has been described as the medium or fluid used for cup actuation, it is to be noted that other "fluids", e.g. silicone, oil, saline, water or other fluids of suitable properties, can also be employed—e.g., a miniature high-rpm electro turbine drive with appropriate fluid path design parameters.

Use

The bi-ventricular assist device 10 is used to maintain blood circulation in a patient whose natural heart is in a state of global fibrillation, cardiac arrest, or bi-ventricular failure. The bi-ventricular assist device 10 may also be used to provide cardiac support for a heart which is functioning at less than normal output or pressure. When it is determined that cardiac support is needed, the surgeon selects bi-ventricular assist device 10 of appropriate size as determined by the size and condition of the patient's heart. The bi-ventricular assist device 10 is inserted over the patient's heart such that ventricles of the heart are fully contained within the assist device 10.

After the assist device 10 is in place, negative pressure is applied to the interior of the cup 12 by the independent vacuum system to help retain the heart within the cup 12. Next, the diaphragm 14 of the ventricular actuation cup 12 is actuated by selectively switching between the systolic pressure source 110 and the diastolic vacuum source 120. The appropriate systolic pressure and diastolic vacuums are determined by measuring the pressure in the pulmonary artery and systemic arterial pressures in the patient. The systolic and diastolic pressures are then adjusted to match the pressures measured in the patient. The measurement of pulmonary artery pressure and systemic arterial pressures is normally accomplished through the placement of catheters within the pulmonary artery and the systemic arteries of the patient.

During use, the diastolic and systolic pressures actually delivered are monitored by placing pressure transducers within the pressure feed system. The output from these transducers is then fed to a monitor which is used to control the flow regulators 140. Since closed-loop feedback systems of this type are well known to those skilled in the art, further discussion of such systems is not necessary.

A significant benefit of the bi-ventricular assist device is that it enables independent right and left ventricular actuation. Under normal physiologic conditions, the right ventricle ejects blood under relatively low pressure into the pulmonary artery. In contrast, the left ventricle ejects the same amount of blood into a high-pressure, high-resistance systemic arterial system. Thus, the normal left ventricle is designed to function as a high-pressure, high-resistance systemic arterial system. Thus, the normal left ventricle is designed to function as a high-pressure pump, while the right ventricle functions as a low-pressure pump. The bi-ventricular assist device 10 can be used to independently control the timing and pressure of the right and left ventricle pumping to optimize forward cardiac output. In contrast, single diaphragm ventricular assist devices, which apply the same person to both the right and left ventricles, cannot achieve optimum cardiac output for both the right and left ventricles. The pressure applied by such devices is, at best, a limiting compromise between right and left ventricular pressures.

The bi-ventricular assist device 10 is particularly useful when abnormal physiological conditions of the heart exist. For example, medically refractory congestive heart failure or cardiogenic shock can occur because of primary right ventricular failure, primary left ventricular failure, simultaneous bi-ventricular failure, or incessant ventricular dysrhythmia such as medically refractory ventricular tachycardia or ventricular fibrillation. In patients with primary left ventricular failure, the pulmonary vascular resistance may be normal to moderately elevated. In contrast, patients with left ventricular failure or biventricular failure may have concomitant pulmonary hypertension. In the severest forms of pulmonary hypertension, right-sided pressures are equal to systemic or left-sided pressures.

Under pathologic conditions, optimal forward cardiac output using the bi-ventricular assist device 10 can be achieved only by controlling independently right and left ventricular systolic actuation as well as diastolic configuration. By incorporating two inflatable chambers within the bi-ventricular assist device 10, systolic actuation of right and left ventricles can occur at differing time intervals and at different compressing pressures. For example, in patients with severe pulmonary hypertension, both left and right ventricular systolic pressures would be equalized. However, in patients with primary left ventricular failure and normal pulmonary vascular resistance, the right ventricle would be compression during mechanical systolic actuation at a slightly longer time interval under normal pressure in order to allow the right ventricle to remain opposed to the septum during left ventricular systolic actuation. By varying the timing of ventricular actuation and by applying appropriate pressure to each ventricle, the inter-ventricular septum will remain in the midline and will not compromise either left or right ventricular systolic emptying or diastolic filling.

The present invention may, of course, be carried out in other specific ways than those herein set forth without parting from the spirit and essential characteristics of the invention. The present embodiments are, therefore, to be considered in all respects as illustrative and not restrictive, and all changes coming within the meaning and equivalency range of the appended Claims are intended to be embraced therein.

What is claimed is:

1. A ventricular assist device, comprising:
   (a) a cup having an open top and defining a heart cavity sized to receive a human heart, said cup being formed of a material with sufficient rigidity to form a self-supporting shell;
   (b) an annular diaphragm disposed along an inner surface of the cup and thereby defining a fluid chamber therebetween;
   (c) a pressure inlet in said cup communicating with said fluid chamber for alternately applying positive and negative pressures to said fluid chamber to actuate said diaphragm, wherein the diaphragm distends to compress the heart when a positive pressure is applied to said fluid chamber, and contracts when negative pressure is applied to said fluid chamber allowing said heart to relax; and
   (d) a size-adjustment assembly to allow for size adjustment of the open top of said cup relative to the human heart inserted into said heart cavity of said cup, said assembly including (i) an inflatable compensation ring adjacent said open top of said cup and positioned between said inner surface of said cup and said diaphragm, (ii) an opening formed in said cup adjacent to said compensation ring, and (iii) a fill valve positioned in said opening and fluid-connectable to said compensation ring to allow fluid to be injected into said compensation ring and thereby inflate the same, whereby the size of said open top of said cup is adjusted.

2. The ventricular assist device of claim 1 further including a constant pressure vacuum port communicating with the interior of said cup.

3. The ventricular assist device of claim 2 further including a flexible seal surrounding said cup opening, said flexible seal extending inwardly from the upper end of said main body section.

4. The ventricular assist device of claim 2 including a plurality of pressure inlets communicating with said fluid chamber, said pressure inlets being circumferentially spaced a fixed distance from the upper end of said main body section.

5. The ventricular assist device of claim 4 further including a drive connector fixed to the end piece of said cup, said drive connector including a center tube communicating with said constant pressure vacuum port, and at least one distribution chamber surrounding said center tube, wherein each said pressure inlets in said main body section is connected by a separate fluid supply line to said distribution chamber in said drive connector.

6. The ventricular actuation device of claim 2, wherein said diaphragm includes a pair of semi-annular diaphragm sections each disposed along a respective portion of said inner surface of said cup, and wherein said fluid chamber includes a pair of semi-annular fluid chamber sections established each established between a respective one of said diaphragm sections and said portion of said inner surface of said cup, said fluid chamber sections being fluid-isolated from one another to allow for independent application of said positive and negative fluid pressures thereto.

7. The ventricular assist device of claim 6 further including a drive connector fixed to said cup, said drive connector including a center tube communicating with said constant pressure vacuum port, and at least one distribution chamber surrounding said center tube, wherein each said pressure inlets in said main body section is connected by a separate fluid supply line to said distribution chamber in said drive connector.

8. The ventricular assist device of claim 7 including two semi-annular distribution chambers surrounding said center tube, each said distribution chamber being connected by said fluid supply lines to respective sets of inlet ports.

9. The ventricular assist device of claim 6 wherein said diaphragms are fixed to the outer surface of said main body section of said cup.

10. A bi-ventricular cardiac assist device comprising:
   (a) a self-supporting cup-shaped outer shell having opposed upper and lower ends and an inner surface which establishes an interior cavity for receiving a heart therein;
   (b) a diametrically opposed pair of slots oriented generally longitudinally between said upper and lower ends of said outer shell;
   (c) a pair of flexible semi-annular diaphragms disposed adjacent to respective semi-annular sections of said inner surface of said outer shell so as to establish a respective pair of fluid chambers between said pair of diaphragms and said semi-annular sections of said inner surface of said outer shell;
   (d) said pair of diaphragms including upper and lower edges wrapped around a respective semi-annular section of said upper and lower ends of said outer shell, and a pair of side edges each inserted through a respective one of said slots, wherein said upper, lower and side edges of said pair of diaphragms are bonded to an exterior surface of said outer shell; and
   (e) a pressure drive system fluid-connected to each one of said pair of fluid chambers for separately and independently pressurizing said pair of fluid chambers to cause separate and independent distention and contraction of said pair of diaphragms.

11. The device of claim 10, wherein said upper, lower and side edges of said pair of diaphragms are bonded to said exterior surface of said outer shell by an isotropic bonding agent which forms a unitary structure between said pair of diaphragms and said outer shell.

12. The device of claim 11, wherein said pair of diaphragms, said outer shell and said isotropic bonding agent are formed of substantially the same urea-linked polyurethane copolymer.

13. The device of claim 11, further comprising a constant pressure vacuum port communicating with the interior cavity of said outer shell.

14. The device of claim 11, further comprising an inflatable compensation ring disposed between said inner surface of said outer shell and said pair of diaphragms.

15. The device of claim 14, further comprising an opening in said outer shell, and a fill valve positioned in said opening and fluid-connectable to said compensation ring to allow fluid to be injected into said compensation ring and thereby inflate the same, whereby the size of said upper end of said shell is adjusted.

16. The device of claim 11, further comprising at least one pair of pressure inlets each communicating with a respective one of said pair of fluid chambers.

17. The device of claim 16, further comprising a plurality of said pressure inlets circumferentially spaced a fixed distance from the upper end of said outer shell.

18. The device of claim 17, further comprising;

a constant pressure vacuum port communicating with the interior cavity of said outer shell, an end piece fixed to said lower end of said outer shell, and a drive connector fixed to said end piece, said drive connector including a center tube communicating with said constant pressure vacuum port, and at least one distribution chamber surrounding said center tube, wherein each of said pressure inlets in said outer shell is connected by a separate fluid supply line to said distribution chamber in said drive connector.

* * * * *

UNITED STATES PATENT AND TRADEMARK OFFICE
CERTIFICATE OF CORRECTION

PATENT NO. : 5,749,839
DATED : May 12, 1998
INVENTOR(S) : Stephen G. KOVACS

It is certified that error appears in the above-identified patent and that said Letters Patent is hereby corrected as shown below:

Column 1, line 12,

--This invention was made with Government support under Grant No.HL48618 awarded by the National Institutes of Health. The Government has certain rights in the invention.--

Signed and Sealed this

Fifth Day of January, 1999

Attest:

Attesting Officer

*Acting Commissioner of Patents and Trademarks*